United States Patent [19]

Pedersen et al.

[11] 4,381,411
[45] Apr. 26, 1983

[54] PRODUCTION OF METHACROLEIN FROM ISOBUTYRALDEHYDE UTILIZING PROMOTED IRON PHOSPHORUS OXIDE CATALYSTS

[75] Inventors: S. Erik Pedersen, Mentor; Louis F. Wagner, Solon, both of Ohio

[73] Assignee: The Standard Oil Company, Cleveland, Ohio

[21] Appl. No.: 276,312

[22] Filed: Jun. 22, 1981

[51] Int. Cl.$^3$ .............................................. C07C 45/32
[52] U.S. Cl. .................................... 568/459; 568/458; 568/470
[58] Field of Search .................... 568/458, 470, 459

[56] References Cited

U.S. PATENT DOCUMENTS

| | | | |
|---|---|---|---|
| 3,207,806 | 9/1965 | Bajars | 568/459 |
| 3,308,194 | 3/1967 | Bajars | 568/459 |
| 3,308,199 | 3/1967 | Bajars | 568/459 |
| 3,329,724 | 7/1967 | Hargis et al. | 568/459 |
| 3,535,400 | 10/1970 | Falbe | 568/459 |
| 3,634,494 | 3/1972 | Tsu | 568/459 |
| 3,649,560 | 3/1972 | Croce | 252/432 |
| 3,652,654 | 3/1972 | Tsu | 560/214 |
| 3,855,279 | 12/1974 | Watkins | 568/459 |
| 3,878,249 | 4/1975 | Gebron et al. | 568/459 |
| 3,917,673 | 11/1975 | Watkins | 560/214 |
| 3,917,712 | 11/1975 | Bouniot et al. | 568/459 |
| 3,948,959 | 4/1976 | Caraterra et al. | 568/459 |
| 3,960,767 | 6/1976 | Christmann | 252/437 |
| 4,077,912 | 3/1978 | Dolhj et al. | 252/461 |

*Primary Examiner*—Werren B. Lone
*Attorney, Agent, or Firm*—Salvatore P. Pace; Herbert D. Knudsen; Larry W. Evans

[57] ABSTRACT

A process is provided for the oxydehydrogenation of aldehydes such as isobutyraldehyde with oxygen in the presence of iron phosphorus oxide catalysts containing promoters selected from Ag, Al, B, Be, Cd, Co, Cr, Cu, Ga, Ge, In, Mn, Ni, Te, Th, Ti, Tl, U, V, Zn, Zr, rare earths and mixtures thereof.

12 Claims, No Drawings

PRODUCTION OF METHACROLEIN FROM ISOBUTYRALDEHYDE UTILIZING PROMOTED IRON PHOSPHORUS OXIDE CATALYSTS

BACKGROUND OF THE INVENTION

This invention relates to the catalytic, oxidative dehydrogenation of isobutyraldehyde to form methacrolein, particularly, using promoted iron phosphorus oxide catalysts.

The dehydrogenation of isobutyraldehyde, a product of the commercial oxo process, to form methacrolein, a monomer in the production of plastics or an intermediate in the preparation of methacrylate monomers, is disclosed in the prior art. For example, U.S. Pat. No. 3,329,724 discloses the production of methacrolein from isobutyraldehyde in the presence of oxides of molybdenum or oxides of uranium. U.S. Pat. Nos. 3,878,249 and 3,917,712 disclose the production of methacrolein by oxidation of isobutyraldehyde in the presence of a silver salt.

The dehydrogenation of aldehydes generally is disclosed in U.S. Pat. Nos. 3,308,194; 3,308,199; 3,649,560 and 3,960,767. Dehydrogenation of aldehydes in the presence of at least two halogens and an inorganic catalyst which may comprise an alkali metal oxide or hydroxide or alkaline earth metal oxide or hydroxide and a metal compound such as iron phosphate, among others, is disclosed in U.S. Pat. No. 3,207,806.

U.S. Pat. No. 3,948,959 discloses the preparation of unsaturated acids by oxidation of the corresponding saturated acid using iron phosphorus oxide catalysts promoted with Li, Na, K, Rb, Cs, Mg, Ca, Sr and Ba. U.S. Pat. Nos. 3,634,494; 3,652,654; 3,855,279; 3,917,673 and and 4,029,695 disclose the preparation of unsaturated acids and esters from saturated acids and esters using iron phosphorus oxide catalysts containing bismuth and/or lead promoters, optionally with other promoter elements, including Mn, U, Pr, Ca, Sr, and Cr. These prior art catalysts characteristically have exhibited short life and thermal instability.

It is therefore an object of the present invention to provide a process for the production of methacrolein from isobutyraldehyde utilizing catalysts having improved activity, improved catalyst life and thermal stability.

SUMMARY OF THE INVENTION

We have found that methacrolein can be produced from isobutyraldehyde in high yields using iron phosphorus oxide catalysts promoted with particular elements. The catalysts used according to the present invention exhibit increased life and thermal stability with respect to prior art iron phosphorus oxide catalysts.

Although promoters such as Mn, U, Cr, were disclosed as being suitable promoters in an iron-lead mixed phosphate system if present in low amounts, and promoters such as Co, Ni, Cu, Zn, Cd and Ce were disclosed for that system as less than suitable promoters, we have found that these elements exhibit excellent promotional activity in the iron phosphorus oxide system for the oxydehydrogenation of isobutyraldehyde when the iron phosphorus oxide catalyst utilized is free of lead phosphate or lead oxide.

In general, the process of the present invention includes the preparation of methacrolein by contacting isobutyraldehyde with molecular oxygen or an oxygen-containing gas in the vapor phase, at a reaction temperature of about 250° C. to 600° C. in the presence of a catalyst having the empirical formula $$A_a Fe_b P_c O_x$$

wherein
A is selected from the group Ag, Al, B, Be, Cd, Co, Cr, Cs, Cu, Ga, Ge, In, Mn, Ni, Te, Th, Ti, Tl, U, V, Zn, Zr, rare earths and mixtures thereof, and wherein
a is about 0.01 to about 2.0
b is about 0.5 to about 2.0
c is about 1.0 to about 3.5 and
x is the number of oxygens needed to satisfy the valence requirements of the remaining elements.

Preferably a equals about 0.15 to 1.5. Also, preferably b is about 1, and c is about 1.5 to 2.

Preferred rare earth metal promoters include La, Ce, Nd, Sm, Eu, Dy, Ho, Tm, Yb and Lu.

DETAILED DESCRIPTION OF THE INVENTION

According to the process of the present invention, isobutyraldehyde is contacted with molecular oxygen in the vapor phase, in the presence of the subject promoted iron phosphorus oxide catalysts. The molecular oxygen is most conveniently added as air, but synthetic streams containing oxygen are also suitable. In addition to the isobutyraldehyde feed and molecular oxygen, other gases may be added to the reactant feed. For example, steam is preferably added to the reactant feed to aid in the reaction, although the mechanism by which it does so is not certain. Inert diluents such as nitrogen, carbon monoxide, carbon dioxide and argon may also be added.

The molar ratio of the reactants may vary widely and are not critical. The ratios of isobutyraldehyde: air: steam are generally in the range of 1:2.5–50:0–50 and are preferably 1:3–10:10–30. Diluents may be present in the range of 0–40 moles per mole of isobutyraldehyde.

The reaction temperature may vary widely and is dependent upon the particular catalyst employed. Normally, temperatures of about 250° to 600° C. are employed with temperatures of about 325° to 475° C. being preferred.

The contact time may vary from a fraction of a second to about 50 seconds. In fixed bed reactions the contact time is preferably about 0.5 seconds to about 10 seconds, for fluid bed, preferably from about 2 seconds to about 20 seconds. The reaction may be conducted at atmospheric, superatmospheric or subatmospheric pressure, preferably from about 1 psia to about 100 psia, most preferably between about 10 to about 30 psia.

The promoted iron phosphorus oxide catalysts of the present invention are represented by the formula set forth above. Preferred promoters include at least one of Cs, Tb, Mn, U, Ag and Tl. These catalysts may be prepared according to methods known in the art.

One method of preparing the catalysts of the present invention includes introducing a compound of iron, and a compound containing the promoter element into water and contacting these with a phosphorus compound; or, the iron and promoter containing compound are introduced into an aqueous solution of phosphoric acid. Preferably, the compounds used containing iron and the promoter elements are soluble in water, and may include salts such as nitrates, halides, sulfates, acetates, carbonates, formates and the like. The resulting solution or slurry is evaporated to dryness, and the resulting solid is calcined at from about 300° to 700° C. Alternatively, the catalyst may be prepared in an organic liquid medium. Alternatively, the aqueous solution or slurry can be adjusted to a pH of about 5-6 before drying.

The catalysts may be formed into tablets, pellets and the like, and may be prepared for use in either fixed or fluid bed reactors. The catalyst may be combined with inert diluents such as silica. Alternately, the catalyst may be coated upon inert supports, such as silica, alumina, alumina-silica, silicon carbide, titania, zirconia, zeolites and clays such as kieselguhr. Techniques of coatings are included in U.S. Pat. No. 4,077,912. The inert supports preferably are of at least about 20 microns in diameter.

The promoted iron phosphorus oxide catalysts utilized in the process of the present invention exhibit high activity for the dehydrogenation of isobutyraldehyde to methacrolein. The catalysts also exhibit long life and thermal stability.

SPECIFIC EMBODIMENTS OF THE INVENTION

Example 1

121.25 grams of $Fe(NO_3)_3.9H_2O$, 40.78 grams $AgNO_3$ and 63.67 grams of 85% $H_3PO_4$ were dissolved in about 300 ml water. The resulting solution was evaporated to a dry paste with heating and stirring. The paste was dried for about 16 hours at 110° C., and the resulting solid was calcined for about 2 hours at 540° C. The solid was crushed and screened to 14-30 mesh (0.595-1.41 mm). The resulting catalyst, $Ag_{0.8}FeP_{1.84}O_x$ was tested for the dehydrogenation of isobutyraldehyde to methacrolein in a 20 cc fixed bed reactor. The reactor consisted of a length of stainless steel tubing having an outer diameter of about 1.3 cm and containing a full length 0.31 cm. diameter axial thermowell. The reactor was heated with a split stainless steel block furnace. Liquid and gaseous products were analyzed by gas chromatography. The test reaction was run at atmospheric pressure. Reaction conditions such as temperature, feed ratios, and contact time are reported in Table I below. Results of the tests reported in the Tables below are reported in terms as follows:

$$\text{Single Pass Yield} = \frac{\text{Moles of methacrolein formed} \times 100}{\text{Moles of isobutyraldehyde fed}}$$

$$\text{Total Conversion} = \frac{\text{Moles of isobutyraldehyde reacted} \times 100}{\text{Moles of isobutyraldehyde fed}}$$

Examples 2-8

Catalysts having the formula $Ag_{0.8}FeP_{1.84}O_x$ were prepared and tested as described in Example 1, under the reaction conditions reported in Table 1. Results of the test reactions are listed in Table I.

Comparative Examples A-C

Catalysts of the formula $FeP_{1.84}O_x$ were prepared as in Example 1, except that the silver component compound was deleted. The catalysts were tested by the procedure of Example 1, with conditions and results being reported in Table 1.

Examples 9-12

Catalysts represented by the formula $Mn_{0.5}FeP_{1.84}O_x$ were prepared and tested according to the procedure of Example 1, except that manganese nitrate was substituted for silver nitrate in the catalyst preparation. Reactions conditions and test results are reported in Table II below.

Comparative Examples D-G

Catalysts of the formula $MnP_{1.84}O_x$ were prepared by adding 172.22 g $Mn(NO_3)_2.6H_2O$ and 63.64 g $H_3PO_4$ to 300 ml water. The resulting solution was evaporated to a dry paste with heating and stirring. The paste was dried for about 16 hours at 110° C. and the resulting solid was calcined for 2 hours at 540° C. The solid was crushed and screened to 14-30 mesh (0.595-1.41 mm) and was tested according to the procedure of Example 1, the reaction conditions and results being reported in Table II.

Comparative Example H

A catalyst of the formula $Ag/SiO_2$ as disclosed in U.S. Pat. No. 3,878,249 was prepared by the following procedure. To 100 ml water was added 47 g $AgNO_3$ and 15.8 g $(NH_4)_2CO_3.H_2O$. The $Ag_2CO_3$ precipitate which was formed was dissolved by adding aqueous ammonia as required (about 25 ml 29% $NH_4OH$). The solution was diluted to 3 liters, and 170 g $SiO_2$ in the form of Aerosil-200 (trademark of Degussa Corp., Teterboro, N.J.) was added. The mixture was evaporated to a dry paste. The paste was dried for about 16 hours at 110° C., and calcined for 2 hours at 540° C.

The resulting solid, (1.65 m moles $Ag/gSiO_2$) was ground and screened to 10 to 14 mesh and was tested according to the procedure of Example 1. The reaction temperature was 400° C., a contact time of 1.06 seconds was used and a hydrocarbon/air/$H_2O$ ratio of 1/7/25. The yield of methacrolein from isobutyraldehyde was 27.4%.

Example 13

A catalyst of the formula $Ag_{0.5}FeP_{1.84}O_x/SiO_2$ (1.65 m moles $Ag/gSiO_2$) was prepared by the procedure of Example H. To 600 ml water was added 121.2 g $Fe(NO_3)_3.9H_2O$, 25.48 g $AgNO_3$, 63.64 g 85% $H_3PO_4$ and 59.91 g $(NH_4)_2CO_3.H_2O$. The precipitate which was formed was substantially dissolved by the addition of 200 ml aqueous ammonia (29% $NH_4OH$) with heating. To this mixture was added 90.91 g $SiO_2$ in the form of Aerosil 200, and the mixture was evaporated to a dry paste. The paste was dried for about 16 hours at 110° C., and calcined for 2 hours at 540° C.

The resulting solid was ground and screened to 10 to 14 mesh and was tested according to the procedure of Example 1 under the reaction conditions of Example H (contact time was 1.04 seconds). The yield of methacrolein from isobutyraldehyde was 53%.

It should be understood that the aldehyde oxydeydrogenation process of the present invention is applicable to the production of unsaturated aldehydes from their corresponding saturated aldehydes, including but not limited to acrolein from propionaldehyde, and crotonaldehyde from n-butyraldehyde.

As is demonstrated by the test results reported in the examples and Tables herein, methacrolein is produced in high yields from isobutyraldehyde according to the process of the present invention, utilizing promoted iron phosphorus oxide catalysts.

Thus it should be apparent to those skilled in the art that the subject invention accomplishes the objects set forth above. It is to be understood that the subject invention is not to be limited by the examples set forth herein. These have been provided merely to demonstrate operability and the selection of iron and phosphorus containing compounds, promoter element containing compounds, preparation techniques, reaction feedstocks and reaction conditions can be determined from the total specification disclosure provided without departing from the spirit of the invention herein disclosed and described, the scope of the invention including modifications and variations that fall within the scope of the attached claims.

TABLE I

OXYDEHYDROGENATION OF ISOBUTYRALDEHYDE TO PRODUCE METHACROLEIN USING $Ag_{0.5}Fe_1P_{1.84}O_x$ CATALYSTS

| Example No. | IBA*/Air/H$_2$O | Temperature (°C.) | Contact Time (Sec) | % Conversion | % Yield Methacrolein |
|---|---|---|---|---|---|
| 1 | 1/5.0/26 | 386 | 0.91 | 99.6 | 59.7 |
| 2 | 1/5.0/26 | 374 | 0.93 | 96.2 | 52.1 |
| 3 | 1/5.0/26 | 394 | 0.90 | 100.0 | 62.7 |
| 4 | 1/5.0/26 | 404 | 0.88 | 100.0 | 64.2 |
| 5 | 1/5.0/26 | 412 | 0.87 | 100.0 | 66.6 |
| 6 | 1/5.0/26 | 435 | 0.83 | 100.0 | 71.6 |
| 7 | 1/5.2/26 | 457 | 0.81 | 100.0 | 76.8 |
| 8 | 1/3.7/26 | 468 | 0.94 | 100.0 | 80.5 |
| A** | 1/7.0/25 | 451 | 0.97 | 100.0 | 32.6 |
| B** | 1/7.0/25 | 395 | 1.05 | 100.0 | 45.8 |
| C** | 1/7.0/27 | 375 | 1.02 | 79.6 | 35.4 |

*IBA = Isobutyraldehyde
**A-C = $FeP_{1.84}O_x$ Catalysts

TABLE II

OXYDEHYDROGENATION OF ISOBUTYRALDEHYDE TO PRODUCE METHACROLEIN USING $Mn_{0.5}Fe_1P_{1.84}O_x$ CATALYSTS

| Example No. | IBA*/Air/H$_2$O | Temperature (°C.) | Contact Time (Sec) | % Conversion | % Yield Methacrolein |
|---|---|---|---|---|---|
| 9 | 1/5.0/26 | 373 | 0.91 | 97.5 | 56.4 |
| 10 | 1/5.0/26 | 396 | 0.88 | 100.0 | 64.5 |
| 11 | 1/5.0/26 | 409 | 0.86 | 100.0 | 67.7 |
| 12 | 1/5.0/12.5 | 405 | 1.51 | 100.0 | 56.1 |
| D** | 1/7.0/25 | 400 | 1.07 | 67.0 | 28.3 |
| E** | 1/7.0/25 | 425 | 1.03 | 88.3 | 38.6 |
| F** | 1/7.0/25 | 475 | 0.95 | 97.3 | 41.1 |
| G** | 1/7.0/13 | 476 | 1.42 | 98.9 | 36.7 |

*IBA = Isobutyraldehyde
**D-G = $MnP_{1.84}O_x$ Catalysts

We claim:

1. A process for the production of methacrolein comprising contacting isobutyraldehyde with molecular oxygen or an oxygen containing gas in the vapor phase at a reaction temperature of about 250° C. to about 600° C. in the presence of a catalyst having the empirical formula $$A_aFe_bP_cO_x$$

wherein
A is selected from the group Ag, Al, Be, Cd, Co, Cr, Cu, Ga, Ge, In, Mn, Ni, Te, Th, Ti, Tl, U, V, Zn, Zr, rare earths and mixtures thereof and wherein
a is about 0.01 to about 2.0
b is about 0.5 to about 2.0
c is about 1.0 to about 3.5 and
x is the number of oxygens needed to satisfy the valence requirements of the remaining elements.

2. A process as in claim 1 wherein isobutyraldehyde is additionally contacted with an inert diluent gas.

3. A process as in claim 1 wherein isobutyraldehyde is additionally contacted with steam.

4. A process as in claim 1 wherein said reaction temperature is within the range of about 325° to about 475° C.

5. A process as in claim 1 wherein the reaction is conducted at a pressure greater than atmospheric pressure.

6. A process as in claim 1 wherein a is about 0.15 to about 1.5.

7. A process as in claim 1 wherein said rare earths are selected from the group consisting of La, Ce, Nd, Sm, Eu, Dy, Ho, Tm, Yb, Lu and mixtures thereof.

8. A process as in claim 1 wherein said catalysts contain silver.

9. A process as in claim 1 wherein said catalyst contains manganese.

10. A process as in claim 1 wherein said catalyst is coated upon a support.

11. A process as in claim 1 wherein b is about 1.

12. A process as in claim 1 wherein c is about 1.5 to about 2.

* * * * *